United States Patent
Norton

(10) Patent No.: US 9,885,803 B2
(45) Date of Patent: ***Feb. 6, 2018

(54) TRANSLUCENT OBJECT PRESENCE AND CONDITION DETECTION BASED ON DETECTED LIGHT INTENSITY

(71) Applicant: Microsoft Technology Licensing, LLC, Redmond, WA (US)

(72) Inventor: Amir A. Norton, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/079,675

(22) Filed: Mar. 24, 2016

(65) Prior Publication Data
US 2016/0202386 A1 Jul. 14, 2016

Related U.S. Application Data

(63) Continuation of application No. 14/199,627, filed on Mar. 6, 2014, now Pat. No. 9,329,304.

(51) Int. Cl.
*G01N 21/958* (2006.01)
*G01V 8/12* (2006.01)
(Continued)

(52) U.S. Cl.
CPC .......... *G01V 8/12* (2013.01); *B23K 26/03* (2013.01); *B23K 26/702* (2015.10); *G01J 1/18* (2013.01);
(Continued)

(58) Field of Classification Search
CPC ............ G01N 21/958; G01J 1/42; G01J 1/18; G01M 11/0221; G01M 11/0278; G01M 1/0221; G01V 8/12
(Continued)

(56) References Cited

U.S. PATENT DOCUMENTS

| | | |
|---|---|---|
| 5,159,402 A | 10/1992 | Ortiz |
| 5,175,594 A | 12/1992 | Campbell |

(Continued)

FOREIGN PATENT DOCUMENTS

| | | |
|---|---|---|
| EP | 1643281 | 4/2006 |
| JP | S5982184 | 5/1984 |

(Continued)

OTHER PUBLICATIONS

"A-GAGE®MINI-Array® Two-Piece Measuring Light Screen Configured for Vehicle Separation 2 Discrete Outputs with EIA-485 Communication Instruction Manual", Available at <Available at: http://info.bannerengineering.com/xpedio/groups/public/documents/literature/117167.pdf>, Apr. 2010, 16 pages.

(Continued)

*Primary Examiner* — Que T Le

(57) ABSTRACT

In embodiments of translucent object presence and condition detection based on detected light intensity, a light is emitted and directed at a first edge of a translucent object along its thickness to pass through the translucent object, such as a lens. An intensity of the light is detected proximate an opposing, second edge of the translucent object. A presence and/or a condition of the translucent object can then be determined based on the detected intensity of the light that passes through the translucent object, where the detected intensity of the light that passes through the translucent object is relative and indicates one of: the presence of the translucent object based on a lower intensity of the light, or the translucent object is not present based on a higher intensity of the light.

20 Claims, 6 Drawing Sheets

(51) Int. Cl.
*G01J 1/18* (2006.01)
*G01J 1/42* (2006.01)
*G01M 11/02* (2006.01)
*G03B 21/20* (2006.01)
*B23K 26/70* (2014.01)
*B23K 26/03* (2006.01)

(52) U.S. Cl.
CPC ........... *G01J 1/42* (2013.01); *G01M 11/0221* (2013.01); *G01M 11/0278* (2013.01); *G01N 21/958* (2013.01); *G03B 21/2086* (2013.01)

(58) Field of Classification Search
USPC .............................................. 250/221, 559.4
See application file for complete search history.

(56) References Cited

U.S. PATENT DOCUMENTS

| | | | |
|---|---|---|---|
| 5,216,481 A | 6/1993 | Minato | |
| 6,201,600 B1 | 3/2001 | Sites et al. | |
| 6,618,136 B1* | 9/2003 | Ishida | G01N 21/94 356/239.1 |
| 6,838,679 B2 | 1/2005 | Ross, III et al. | |
| 6,914,247 B2 | 7/2005 | Duggan et al. | |
| 9,329,304 B2 | 5/2016 | Norton | |
| 2009/0303488 A1 | 12/2009 | Smith | |
| 2015/0253456 A1 | 9/2015 | Norton et al. | |

FOREIGN PATENT DOCUMENTS

| | | |
|---|---|---|
| JP | S6066226 | 4/1985 |
| WO | WO-2007130313 | 11/2007 |

OTHER PUBLICATIONS

"International Search Report and Written Opinion", Application No. PCT/US2015/017869, dated Jul. 17, 2015, 12 pages.

"Non-Final Office Action", U.S. Appl. No. 14/199,627, dated Aug. 10, 2015, 7 pages.

"Notice of Allowance", U.S. Appl. No. 14/199,627, dated Dec. 14, 2015, 7 pages.

"Second Written Opinion", Application No. PCT/US2015/017869, dated Feb. 15, 2016, 7 pages.

"International Preliminary Report on Patentability Issued in PCT Application No. PCT/US2015/017869", dated Jun. 16, 2016, 8 Pages.

\* cited by examiner

TRANSLUCENT OBJECT PRESENCE AND CONDITION DETECTION BASED ON DETECTED LIGHT INTENSITY

RELATED APPLICATION

This application is a continuation of and claims priority to U.S. patent application Ser. No. 14/199,627 filed Mar. 6, 2014 entitled "Object Presence and Condition Detection," the disclosure of which is incorporated by reference herein in its entirety.

BACKGROUND

Consumer electronics, such as a gaming system or device, may use a high-powered laser and the intensity of the laser light is reduced through the use of various lenses and/or translucent material so that the laser light is safe to shine on a person, such as on a person's face for detection and recognition implementations. If a lens or the translucent material is missing, has a hole or crack in it, or is otherwise damaged, the laser light may not be properly diffused and the intensity of the light can cause an eye injury to a user of the device. In various systems and devices, safety compliance features are implemented to verify the presence and condition of the lenses so as to avoid a laser causing eye damage, which can occur in just a matter of milliseconds. However, conventional techniques do not directly measure the presence or condition of the lenses, but rather detect a proxy component and infer the condition of the lenses. This can potentially result in false inferences, since the proxy does not guarantee that a lens was even installed in the first place, or that it was free of damage when it was installed.

SUMMARY

This Summary introduces features and concepts of object presence and condition detection, which is further described below in the Detailed Description and/or shown in the Figures. This Summary should not be considered to describe essential features of the claimed subject matter, nor used to determine or limit the scope of the claimed subject matter.

Object presence and condition detection is described. In embodiments, a light is emitted that is directed at a first edge of a translucent object to pass through the translucent object, such as a lens. An intensity of the light is detected proximate an opposing, second edge of the translucent object. A presence and/or a condition of the translucent object can then be determined based on the detected intensity of the light that passes through the object. The translucent object can be implemented as a multi-lens array, and a laser light is directed through optic surfaces of the multi-lens array with a laser. The presence and the condition of the multi-lens array can be continuously determined as a safety compliance of the laser light being directed through the multi-lens array.

In implementations, the detected intensity of the light that passes through the translucent object is relative, and can indicate the presence of the object based on a higher intensity of the light, or the object is not present based on a lower intensity of the light. Additionally, the detected intensity of the light that passes through the translucent object can indicate a damaged condition of the object, such as when the detected intensity of the light is approximately that of the lower intensity of the light. An object detection application can be implemented as part of a system that includes a light emitter, the translucent object, and a light detector. The object detection application can receive a voltage signal from the light detector, where the voltage signal is variable and corresponds to the detected intensity of the light that passes through the translucent object. The object detection application can then determine the presence and/or the condition of the translucent object based on the received voltage signal. The voltage signal may be one of above or below a voltage comparison threshold, or can be comparable to a light emission signature of the translucent object.

BRIEF DESCRIPTION OF THE DRAWINGS

Embodiments of object presence and condition detection are described with reference to the following Figures. The same numbers may be used throughout to reference like features and components that are shown in the Figures.

DETAILED DESCRIPTION

Embodiments of object presence and condition detection are described and can be implemented to continuously and in real-time detect the presence and/or condition of a translucent object, such as a lens. In implementations, a light emitter directs a light at an edge of a translucent object to pass through the object. An intensity of the light is detected by a light detector at an opposing edge of the translucent object, and the presence and/or condition of the object can then be determined based on the detected intensity of the light that passes through the translucent object.

In a system, the translucent object can be implemented as a multi-lens array, and a laser light is directed through optic surfaces of the multi-lens array with a laser. The light emitter directs the emitted light through the multi-lens array from one edge to another in a direction perpendicular to an axis of the optic surfaces of the multi-lens array. The emitted light is non-intrusive to the function of the multi-lens array and does not interfere with the projection of the laser light. The presence and the condition of the multi-lens array can be continuously determined as a safety compliance feature when using the laser light that is directed through the optic surfaces of the multi-lens array.

While features and concepts of object presence and condition detection can be implemented in any number of different devices, systems, networks, environments, and/or configurations, embodiments of object presence and condition detection are described in the context of the following example devices, systems, and methods.

Figure 1:
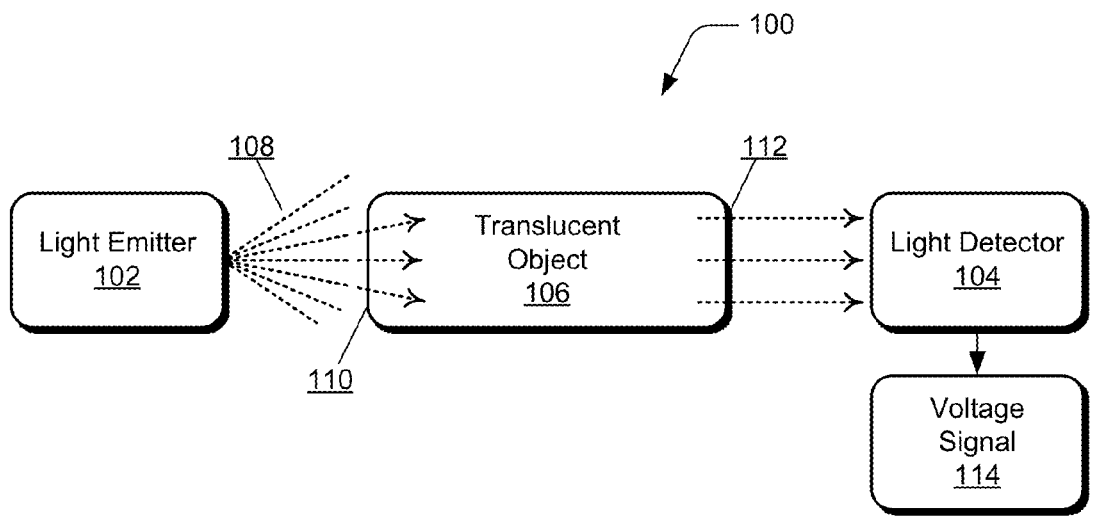
FIG. 1 illustrates an example system in which embodiments of object presence and condition detection can be implemented.

FIG. 1 illustrates an example system 100 in which embodiments of object presence and condition detection can be implemented. The system 100 includes a light emitter 102, a light detector 104, and a translucent object 106. The light emitter 102 can be implemented as any type of light source, such as a light emitting diode (LED), that emits a light 108, which is directed at a first edge 110 of the translucent object. The light emitter 102 can be implemented as one or more LEDs or other types of lights in the visible light spectrum, or in the infra-red (IR) light spectrum. The emitted light 108 is directed to pass through the translucent object 106 and the light detector 104 detects an intensity of the light proximate an opposing, second edge 112 of the translucent object. A presence and/or a condition of the translucent object 106 can then be determined based on the detected intensity of the light that passes through the object. The intensity of the light after traveling through the translucent object 106, as measured by the light detector 104, will be different depending on the presence and condition of the object, and a variable detector output can provide the presence and condition information in continuous real-time.

The light detector 104 can be implemented as a photo transistor, optical detector, or any type of transducer that has sensitivity to the wavelengths generated by the light emitter and that converts the light intensity to another signal form, such as to generate a voltage signal 114 corresponding to the detected intensity of the light 108 that passes through the translucent object. The presence and/or the condition of the translucent object 106 can be based on the voltage signal, which may be determined as being above or below a voltage comparison threshold, or can be comparable to a light emission signature of the translucent object.

Generally, the translucent object 106 can be any type of object that is transparent or semi-transparent allowing light to pass through, much like a waveguide, and may be implemented as any type of optic lens, lens system, or other object having any shape, color, and/or configuration. The translucent object 106 acts as a waveguide and concentrates the light emitter's divergent light beams, which can produce a higher intensity light at the light detector 104 than would otherwise occur if the translucent object was not present in the system. Any damage to the translucent object, such as a hole, a crack, or other type of damage, will reduce the passage of light through the object and thus reduce the intensity of light that the light detector receives. Therefore, to detect a high-enough intensity of the light at the light detector 104 to signal an acceptable condition, the translucent object 106 must be present (e.g., for the light 108 to pass through), and not damaged, which reduces the intensity of the light that can be detected. In alternate implementations, a light emitter 102 that emits a directed light can be utilized and the light is detected at a higher intensity by the light detector 104 if the translucent object 106 is not present. The intensity of the detected light may then be lower when the translucent object 106 is present due to dissipation of the light as it passes through the object.

In various implementations, the translucent object 106 may be implemented as a multi-lens array as described with reference to FIG. 3. The translucent object 106 may also be implemented as an optic lens as described with reference to FIG. 4. The translucent object 106 may also be implemented as a combination of objects as described with reference to FIGS. 7 and 8. In the lens implementations, the light emitter 102 and the light detector 104 are aligned with the width (e.g., the thickness) of a lens, as opposed to the functional direction of a lens. For example, the light emitter 102 directs the emitted light 108 through a lens from one edge to another in a direction perpendicular to an axis of the optic surfaces of the lens, and the emitted light is non-intrusive to the function of a lens. In other implementations, techniques of the example system 100 may be implemented for any number of scenarios, such as in a tamper proof device to check that some component has not been removed, in a camera system to check that a lens has not been removed or has been installed, or in any type of system or device replacing a mechanical switch or for other fail-safe component checks.

Example methods 200 and 600 are described with reference to respective FIGS. 2 and 6 in accordance with one or more embodiments of object presence and condition detection. Generally, any of the components, modules, methods, and operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like.

Figure 2:
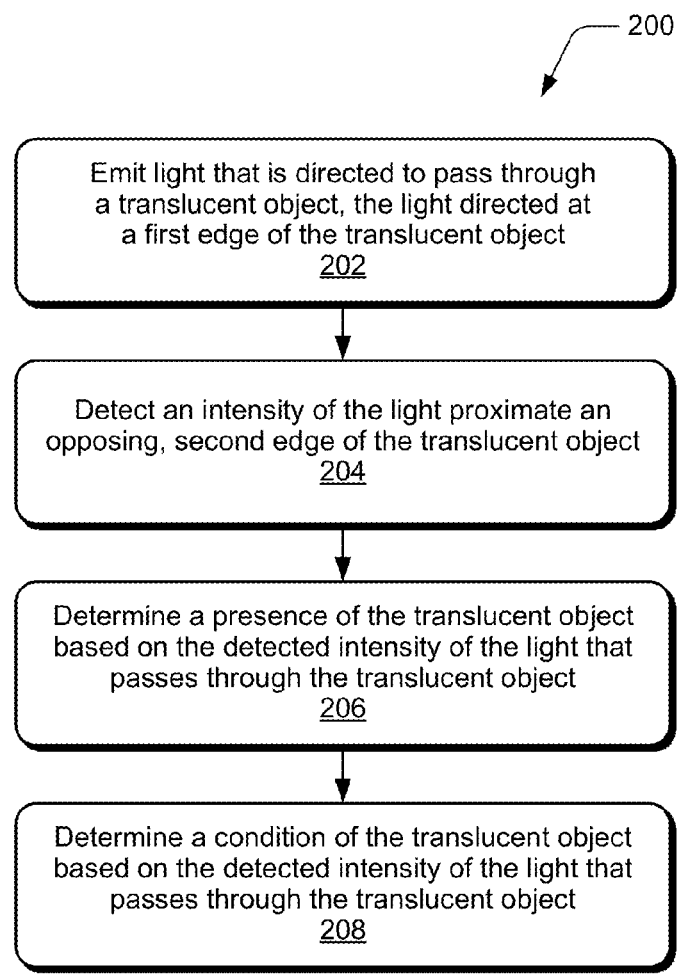
FIG. 2 illustrates example method(s) of object presence and condition detection in accordance with one or more embodiments.

FIG. 2 illustrates example method(s) 200 of object presence and condition detection, and is generally described with reference to the example system 100 shown in FIG. 1. The order in which the method is described is not intended to be construed as a limitation, and any number or combination of the method operations can be performed in any order to implement a method, or an alternate method.

At 202, light is emitted and directed to pass through a translucent object, and the light is directed at a first edge of the translucent object. For example, the light emitter 102 emits the light 108 that is directed at the first edge 110 of the translucent object 106 to pass through the object. At 204, an intensity of the light is detected proximate an opposing, second edge of the translucent object. For example, the light detector 104 detects an intensity of the light proximate the opposing, second edge 112 of the translucent object 106.

At 206, a presence of the translucent object is determined based on the detected intensity of the light that passes through the translucent object. For example, the light detector 104 converts the detected intensity of the light 108 into the voltage signal 114 from which the presence of the translucent object 106 can be determined. In implementations, the detected intensity of the light is relative and indicates the presence of the translucent object based on a higher intensity of the light, or the translucent object is not present based on a lower intensity of the light. For example, the translucent object 106 acts as a waveguide and concentrates the light, which is detected as a higher intensity of the light at the light detector 104, resulting in a lower voltage signal. If the translucent object 106 is not present in the system, then the light can be detected at a lower intensity of the light at the light detector 104, resulting in a higher voltage signal. Alternatively, the system may be implemented so that the detected intensity of the light indicates the presence of the translucent object based on a lower intensity of the light (e.g., and/or a lower voltage signal), or the translucent object is not present based on a higher intensity of the light (e.g., and/or a higher voltage signal).

At 208, a condition of the translucent object is determined based on the detected intensity of the light that passes through the translucent object. For example, the light detector 104 converts the detected intensity of the light 108 into the voltage signal 114 from which the condition of the translucent object 106 is determined. Any damage to the translucent object, such as a hole, a crack, or other type of damage, will reduce the passage of light through the object and thus reduce the intensity of light that the light detector 104 receives. If the translucent object is damaged, or otherwise not in an operable condition, then the light will be detected at a lower intensity at the light detector 104, resulting in a higher voltage signal, similar to when the translucent object is not present in the system.

Figure 3:
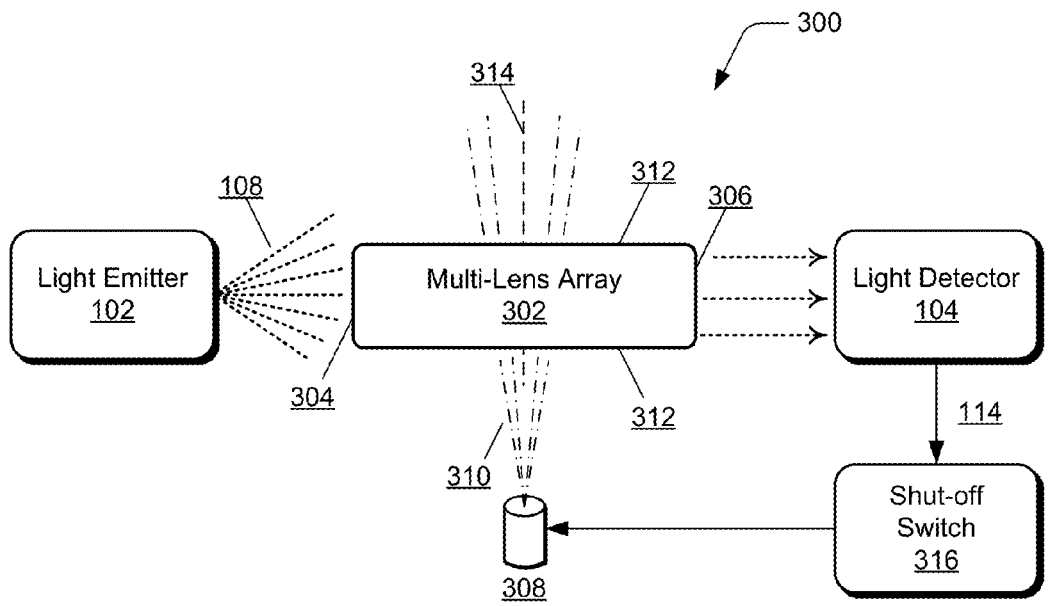
FIG. 3 illustrates an implementation of the example system in which embodiments of object presence and condition detection can be implemented.

FIG. 3 illustrates an example system 300 in which embodiments of object presence and condition detection can be implemented. The system 300 includes the light emitter 102 and the light detector 104 as described with reference to FIG. 1. The system 300 also includes a multi-lens array 302, which is an example of a translucent object, through which the light emitter 102 emits the light 108, which is directed at a first edge 304 of the multi-lens array. The emitted light 108 is directed to pass through the multi-lens array 302 and the light detector 104 detects an intensity of the light proximate an opposing, second edge 306 of the multi-lens array. The light emitter 102 and the light detector 104 are aligned with the width (e.g., the thickness) of the multi-lens array 302, as opposed to the functional direction of the multi-lens array.

The example system 300 also includes a laser 308 that directs a laser light 310 through optic surfaces 312 of the multi-lens array 302. The light emitter 102 directs the light 108 through the multi-lens array from the first edge 304 to the second edge 306 in a direction perpendicular to an axis 314 of the optic surfaces 312 of the multi-lens array. The emitted light 108 is non-intrusive to the function of the multi-lens array 302 and does not interfere with the projection of the laser light. The presence and the condition of the multi-lens array can be continuously determined based on the detected intensity of the light that passes through the multi-lens array, and as a safety compliance feature when using the laser light that is directed through the optic surfaces of the multi-lens array.

The light detector 104 converts the detected light intensity to another signal form (e.g., the voltage signal 114) that corresponds to the detected intensity of the light 108 that passes through the multi-lens array. The voltage signal 114 that indicates the presence and/or the condition of the multi-lens array 302 can be input to an emergency shut-off switch 316 that turns off the laser 308 if the multi-lens array is determined not to be present in the system, is damaged, or is in some other inoperable condition. The example system 300 has a fast response time (e.g., on the order of microseconds) to detect and signal the emergency shut-off switch 316, and prevent potential injury that may be caused by the laser light. The system is applicable and can be implemented for any consumer device that may require a similar safety compliance feature.

Figure 4:
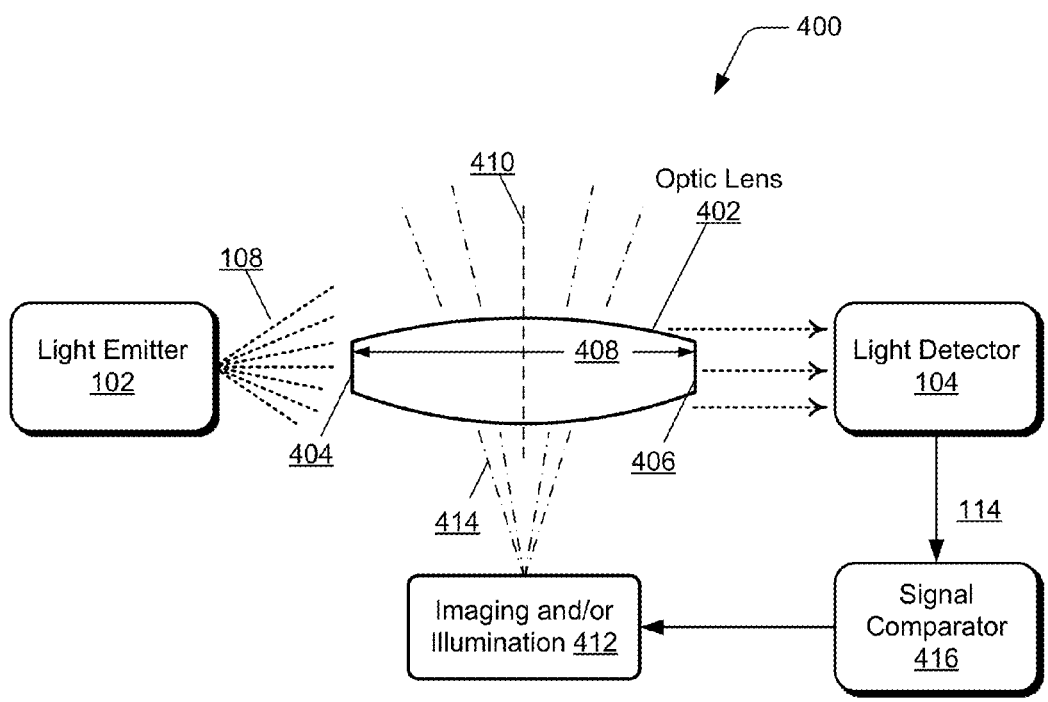
FIG. 4 illustrates an implementation of the example system in which embodiments of object presence and condition detection can be implemented.

FIG. 4 illustrates an example system 400 in which embodiments of object presence and condition detection can be implemented. The system 400 includes the light emitter 102 and the light detector 104 as described with reference to FIG. 1. The system 400 also includes an optic lens 402, which is an example of a translucent object, through which the light emitter 102 emits the light 108, which is directed at a first edge 404 of the lens. The emitted light 108 is directed to pass through the lens 402 and the light detector 104 detects an intensity of the light proximate an opposing, second edge 406 of the lens. The light emitter 102 and the light detector 104 are aligned with the width (e.g., the thickness) of the lens 402, as opposed to the functional direction of the lens. The light emitter 102 directs the light 108 through the lens from the first edge 404 to the second edge 406 along a diameter 408 of the lens and in a direction perpendicular to an axis 410 of the optic surfaces of the lens.

The example system 400 can also include any type of imaging and/or illumination component 412 that directs light 414 through the lens, or receives the light 414 through the lens. The emitted light 108 is non-intrusive to the function of the optic lens 402 and does not interfere with the light 414 that is directed and/or received through the optic surfaces of the lens. The presence and the condition of the lens 402 can be continuously determined based on the detected intensity of the light that passes through the lens. The light detector 104 converts the detected light intensity to another signal form (e.g., the voltage signal 114) that corresponds to the detected intensity of the light 108 that passes through the lens. The voltage signal 114 that indicates the presence and/or the condition of the lens 402 can then be input to a signal comparator 416 that controls the imaging and/or illumination component 412 based on whether the lens is determined to be present or not in the system, is damaged, or is in some other inoperable condition. The example system 400 is applicable and can be implemented for any consumer device, such as to detect the presence of a lens in an interchangeable lens system, to detect not only that a translucent object has been installed, but that the object has been installed correctly, and/or for any other user operability verification and/or safety check.

Figure 5:
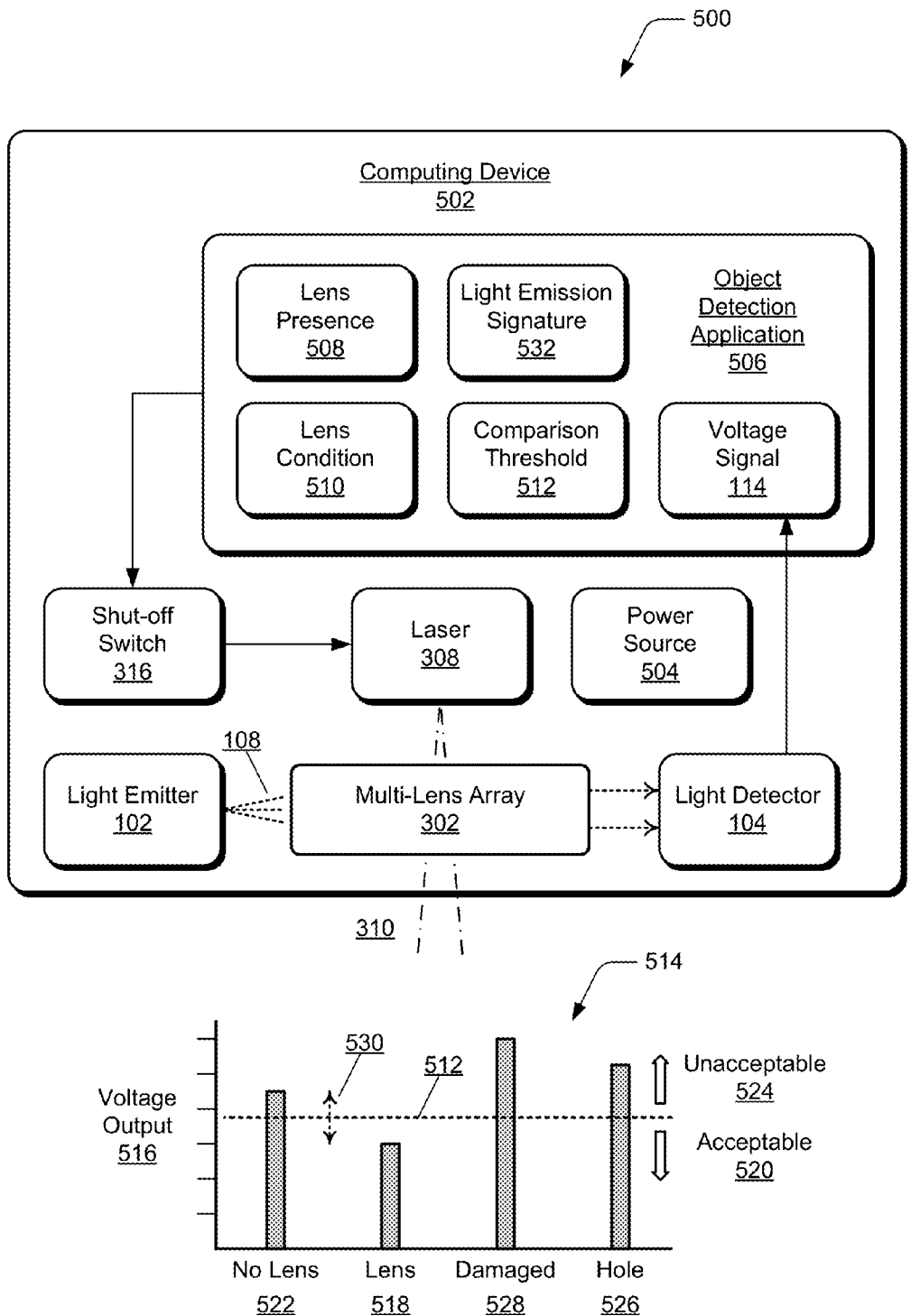
FIG. 5 illustrates an example system in which embodiments of object presence and condition detection can be implemented.

FIG. 5 illustrates an example system 500 in which embodiments of object presence and condition detection can be implemented. The system 500 includes an example computing device 502 that may be any one or combination of a wired or wireless device, such as a mobile phone, tablet, computing, communication, entertainment, gaming, media playback, desktop computer, and/or other type of device implemented as a computing device. For example, the computing device 502 may be a gaming device, or a component of a gaming system, and include the example system 300 as shown and described with reference to FIG. 3. The computing device 502 can include a wired and/or battery power source 504 to power the components, such as the light emitter 102, the light detector 104, the multi-lens array 302, and the laser 308 that generates the laser light 310. Any of the devices described herein, such as the computing device 502, can be implemented with various components, such as a processing system and memory, as well as any number and combination of differing components as further described with reference to the example device shown in FIG. 9.

The computing device 502 includes an object detection application 506 that can be implemented as a software application (e.g., executable instructions) stored on a computer-readable storage memory, such as any suitable memory device or electronic data storage. The computing device 502 can be implemented with a computer-readable storage memory as described with reference to the example device shown in FIG. 9. Additionally, the computing device can be executed with a processing system to implement embodiments of object presence and condition detection, as described herein.

In embodiments, the object detection application 506 is implemented to receive the voltage signal 114 from the light detector 104, from which the object detection application can determine lens presence 508 and/or a lens condition 510 (e.g., of the multi-lens array 302). The light detector 104 converts the detected light intensity into the voltage signal 114 that corresponds to the detected intensity of the light 108 that passes through the multi-lens array 302. The presence 508 and/or the condition 510 of the multi-lens array can be continuously determined by the object detection application 506 as a safety compliance feature when using the laser light that is directed through the optic surfaces of the multi-lens array.

In an embodiment, the object detection application 506 is implemented to compare the variable voltage signal 114 to a voltage comparison threshold 512 to determine the lens presence 508 and/or the lens condition 510 of the multi-lens array 302. An example 514 illustrates the voltage comparison threshold 512 based on a voltage output 516 (e.g., the voltage signal) from the light detector 104. In this example, an undamaged lens (e.g., the multi-lens array 302) that is present in the system at 518 results in a lower voltage output that is below the voltage comparison threshold 512, which indicates an operating condition of the lens is acceptable at 520. As described earlier with reference to the example systems, the multi-lens array 302 can act as a waveguide and concentrate the emitted light 108, which is detected as a higher intensity of the light at the light detector 104, resulting in the lower voltage output that indicates an operating condition of the multi-lens array is acceptable.

The example 514 further illustrates that a lens missing from the system at 522 (e.g., no lens) results in a higher voltage output that is above the voltage comparison threshold 512, which indicates an operating condition of the lens that is unacceptable at 524. As described earlier, if the multi-lens array 302 is not present in the system, then the emitted light 108 is detected at a lower intensity of the light at the light detector 104, resulting in the higher voltage output that indicates the operating condition of the multi-lens array is unacceptable. Based on a determination of the unacceptable operating condition, the object detection application 506 can initiate turning off the laser 308, such as by signaling the shut-off switch 316.

Similarly, the example 514 illustrates that damage to the multi-lens array 302 results in a higher voltage output that is above the voltage comparison threshold 512, such as if the multi-lens array has a hole in it at 526 or is otherwise damaged at 528 (e.g., has been cracked or grooved). The higher voltage outputs that are above the voltage comparison threshold 512 indicate that the operating condition of the multi-lens array is unacceptable. In this implementation, any of the unacceptable operating conditions drive the voltage output 516 in the same direction, as voltage outputs that are higher than the voltage comparison threshold 512, thus making it simple for the object detection application 506 to compare the voltage signal 114 against the comparison threshold 512 and distinguish the unacceptable operating conditions from an acceptable operating condition.

Although the voltage comparison threshold 512 is shown and described as a single voltage output level, the voltage comparison threshold 512 may also be implemented as a voltage comparison range 530, such as shown in the example 514. The voltage comparison threshold 512 and/or the voltage comparison range 530 can be established based on characterizing hundreds of similar lenses or translucent objects, and determining a typical voltage range of the voltage signal 114 that is output from the light detector 104. In similar implementations, the object detection application 506 can detect the condition in which the multi-lens array 302 is present and undamaged in the system, yet has been installed upside-down, based on a voltage signal that is similar to when the multi-lens array is missing from the system.

In other systems and implementations, the presence and/or the condition of the multi-lens array 302 can be based on a comparison of the voltage signal 114 to a light emission signature 532 of the multi-lens array. For example, the emitted light 108 that passes through a translucent object may be detected based on a unique geometry and/or configuration of the object, and the light that is detected by the light detector 104 is a unique light emission signature 532 of the particular object. In the computing device 502, the multi-lens array 302 of the example system 300 can be initially calibrated to determine its light emission signature 532. The object detection application 506 can then continuously and in real-time determine the presence and/or the condition of the multi-lens array 302 based a comparison of the light emission signature 532 to the voltage signal 114 that is received from light detector 104.

Figure 6:
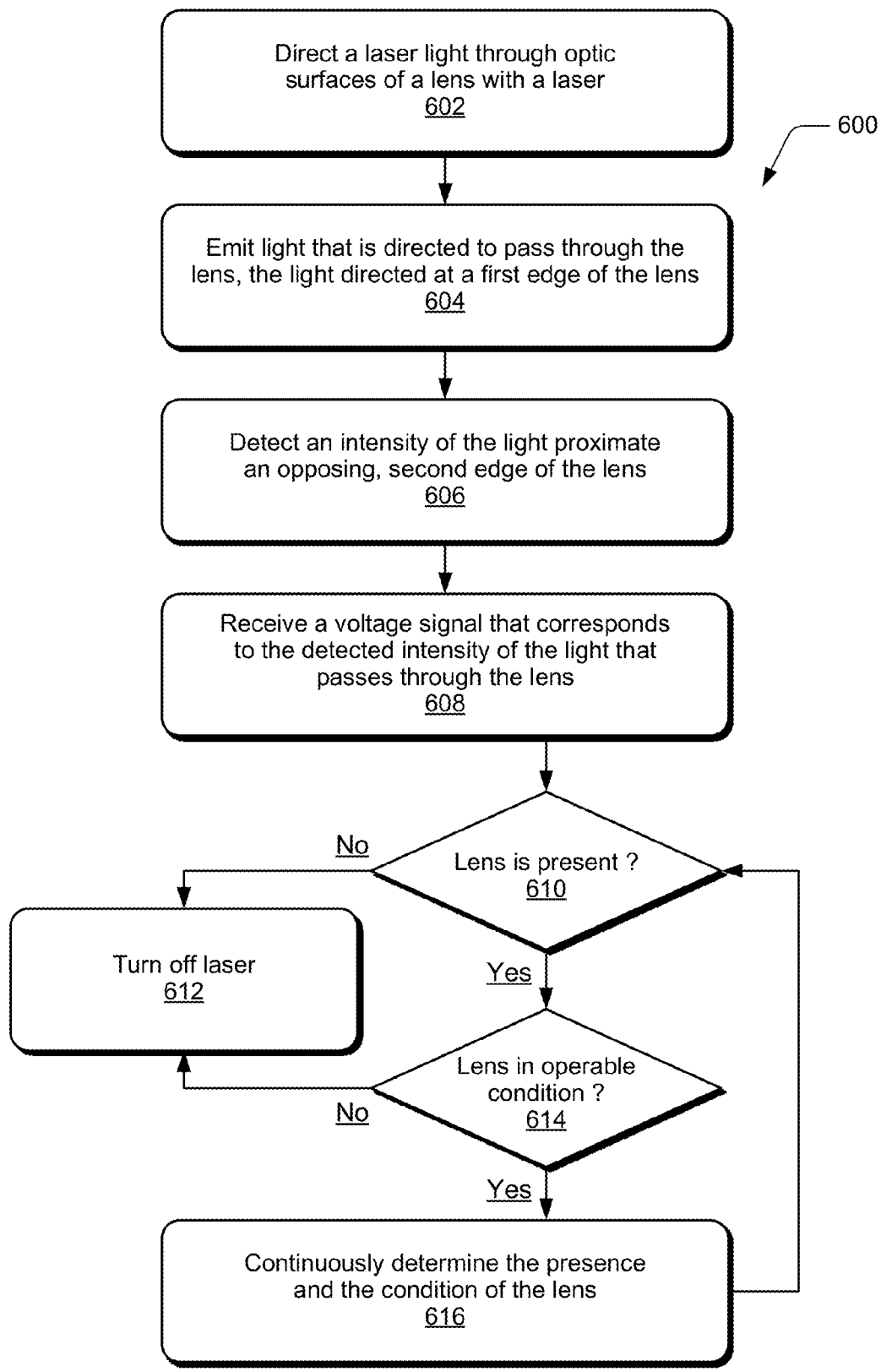
FIG. 6 illustrates example method(s) of object presence and condition detection in accordance with one or more embodiments.

FIG. 6 illustrates example method(s) 600 of object presence and condition detection, and is generally described with reference to the example system 500 shown in FIG. 5. The order in which the method is described is not intended to be construed as a limitation, and any number or combination of the method operations can be performed in any order to implement a method, or an alternate method.

At 602, a laser light is directed through optic surfaces of a lens with a laser. For example, the laser 308 that is implemented in the computing device 502 (FIG. 5) generates the laser light 310 that is directed through the optic surfaces 312 (FIG. 3) of the multi-lens array 302. At 604, light is emitted and directed to pass through the lens, and the light is directed at a first edge of the lens. For example, the light emitter 102 emits the light 108 that is directed at the first edge 304 of the multi-lens array 302 to pass through the multi-lens array.

At 606, an intensity of the light is detected proximate an opposing, second edge of the lens. For example, the light detector 104 detects an intensity of the light 108 proximate the opposing, second edge 306 of the multi-lens array 302. In the example systems, a lens can be implemented as the multi-lens array 302 as shown in FIGS. 3 and 5, or as the optic lens 402 shown in FIG. 4, and the light 108 is emitted and directed to pass through along the diameter 408 of the optic lens and perpendicular to the axis 410 of the lens. The detected intensity of the light that passes through any of the translucent objects is relative and can indicate the presence of an object based on a higher intensity of the light, or that the object is not present based on a lower intensity of the light. Alternatively, systems may be implemented to determine the presence of a translucent object based on a lower intensity of the light, or that the object is not present based on a higher intensity of the light.

At 608, a voltage signal is received that corresponds to the detected intensity of the light that passes through the lens. For example, the object detection application 506 that is implemented by the computing device 502 receives the voltage signal 114, and the object detection application can determine the presence and/or the condition of the multi-lens array 302 based on the voltage signal that corresponds to the detected intensity of the light.

At 610, a determination is made as to whether the lens is present based on the detected intensity of the light that passes through the lens. For example, the object detection application 506 determines the presence of the multi-lens array 302 in the system based on the voltage signal 114 being one of above or below the voltage comparison threshold 512, or the object detection application 506 compares the voltage signal 114 to the light emission signature 532 of the multi-lens array.

If the lens is not present, such as having been removed or is broken out (i.e., "no" from 610), then at 612, the laser is turned off. For example, the object detection application 506 initiates turning off the laser 308, such as by signaling the shut-off switch 316. If the lens is present (i.e., "yes" from 610), then at 614, a determination is made as to whether the lens is in an operable condition based on the detected intensity of the light that passes through the lens. For example, the object detection application 506 determines whether the multi-lens array 302 is in an operable condition based on the voltage signal 114 that corresponds to the detected intensity of the light, which indicates a damaged condition of the multi-lens array if the detected intensity is approximately that of the lower intensity of the light.

If the lens is not in an operable condition, such as having been cracked or otherwise damaged (i.e., "no" from 614), then at 612, the laser is turned off. For example, the object detection application 506 initiates turning off the laser 308, such as by signaling the shut-off switch 316. If the lens is in an operable condition (i.e., "yes" from 614), then at 616, the presence and the condition of the lens is continuously determined in real-time as a safety compliance when the laser light is directed through the lens. Accordingly, the method continues at 610 to determine whether the lens (e.g., the multi-lens array 302) is present and at 614 to determine whether the lens is in an operable condition based on the detected intensity of the light that passes through the lens.

Figure 7:
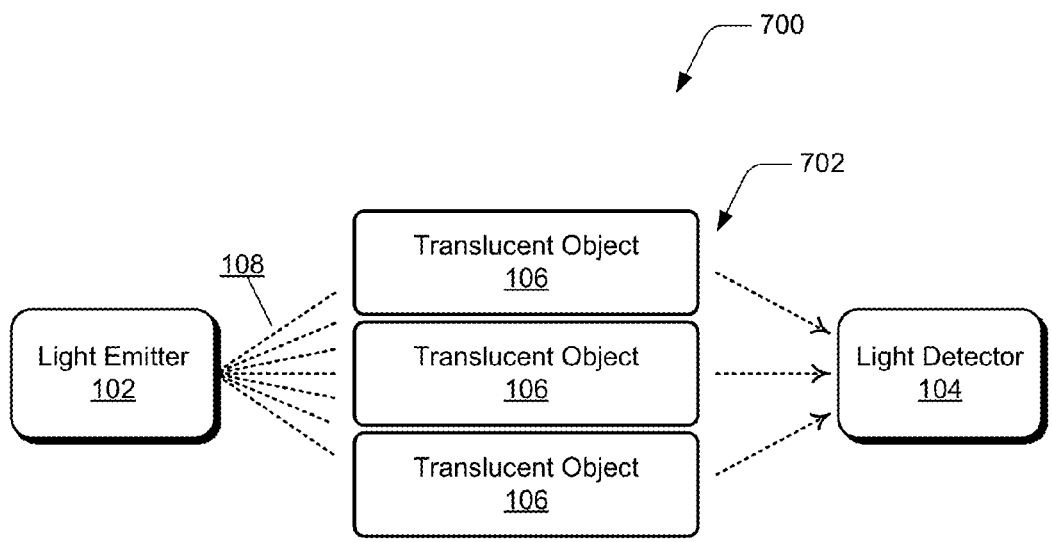
FIG. 7 illustrates an implementation of the example system in which embodiments of object presence and condition detection can be implemented.

FIG. 7 illustrates an example system 700 in which embodiments of object presence and condition detection can be implemented. The system 700 includes the light emitter 102 and the light detector 104 as described with reference to FIG. 1. The system 700 also includes multiple translucent objects 106 in a stacked configuration 702 through which the light emitter 102 emits the light 108. The emitted light 108 is directed to pass through the translucent objects 106 and the light detector 104 detects an overall intensity of the light that passes through the stacked configuration 702 of the translucent objects. The example system 700 illustrates that one set of the light emitter 102 and light detector 104 components can be implemented for multiple translucent objects.

Figure 8:
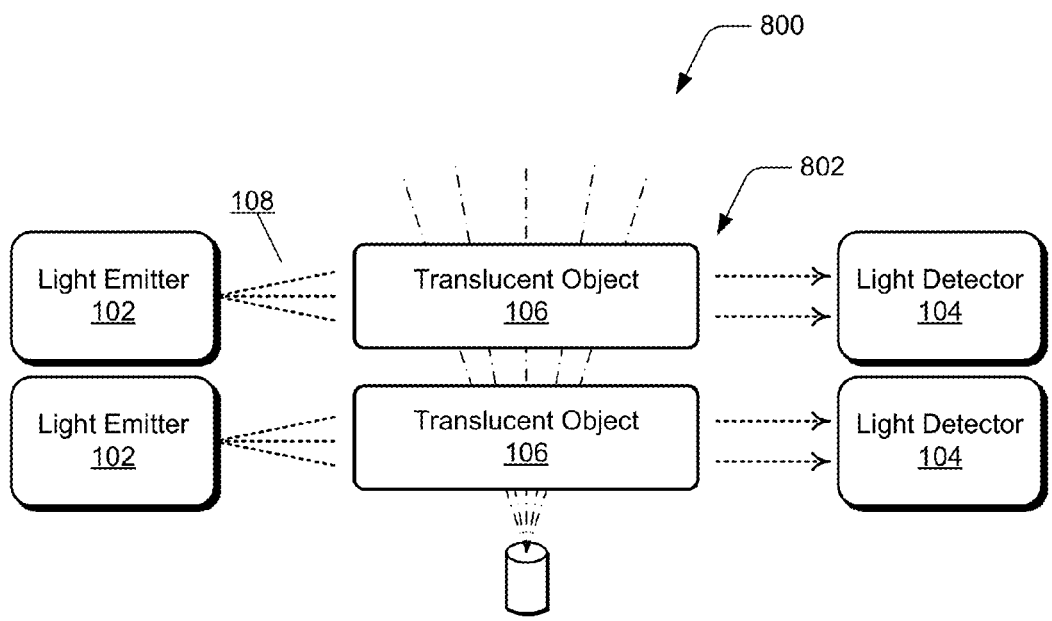
FIG. 8 illustrates an implementation of the example system in which embodiments of object presence and condition detection can be implemented.

FIG. 8 illustrates an example system 800 in which embodiments of object presence and condition detection can be implemented. The system 800 includes a similar stack configuration 802 of the translucent objects 106 as described with reference to FIG. 1. The example system 800 illustrates that, for multiple translucent objects, each translucent object is implemented with an associated set of the light emitter 102 and light detector 104 components. Each light emitter 102 emits the light 108 that is directed to a particular one of the translucent objects 106, and a corresponding light detector 104 detects the intensity of the light that passes through the particular, associated translucent object.

Figure 9:
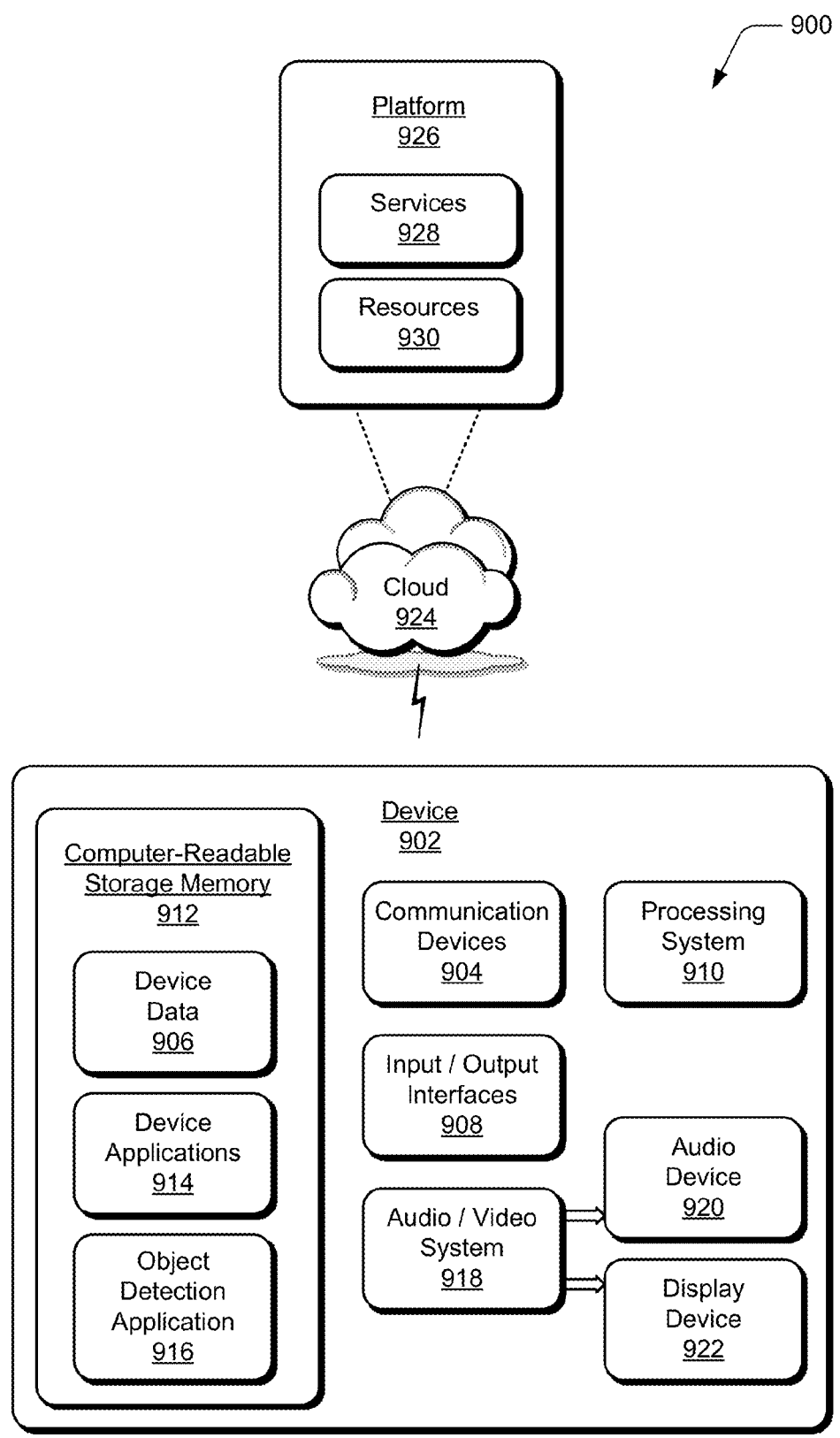
FIG. 9 illustrates an example system with an example device that can implement embodiments of object presence and condition detection.

FIG. 9 illustrates an example system 900 that includes an example device 902, which can implement embodiments of object presence and condition detection. The example device 902 can be implemented as any of the computing devices described with reference to the previous FIGS. 1-8, such as any type of client device, mobile phone, tablet, computing, communication, entertainment, gaming, media playback, and/or other type of device. For example, the computing device 502 shown in FIG. 5 may be implemented as the example device 902.

The device 902 includes communication devices 904 that enable wired and/or wireless communication of device data 906, such as object presence and condition determination information, voltage comparison threshold values, and light emission signatures of the various translucent objects, lenses, and multi-lens arrays. Additionally, the device data can include any type of audio, video, and/or image data. The communication devices 904 can also include transceivers for cellular phone communication and for network data communication.

The device 902 also includes input/output (I/O) interfaces 908, such as data network interfaces that provide connection and/or communication links between the device, data networks, and other devices. The I/O interfaces can be used to couple the device to any type of components, peripherals, and/or accessory devices. The I/O interfaces also include data input ports via which any type of data, media content, and/or inputs can be received, such as user inputs to the device, as well as any type of audio, video, and/or image data received from any content and/or data source.

The device 902 includes a processing system 910 that may be implemented at least partially in hardware, such as with any type of microprocessors, controllers, and the like that process executable instructions. The processing system can include components of an integrated circuit, programmable logic device, a logic device formed using one or more semiconductors, and other implementations in silicon and/or hardware, such as a processor and memory system implemented as a system-on-chip (SoC). Alternatively or in addition, the device can be implemented with any one or combination of software, hardware, firmware, or fixed logic circuitry that may be implemented with processing and control circuits. The device 902 may further include any type of a system bus or other data and command transfer system that couples the various components within the device. A system bus can include any one or combination of different bus structures and architectures, as well as control and data lines.

The device 902 also includes a computer-readable storage memory 912, such as data storage devices that can be accessed by a computing device, and that provide persistent storage of data and executable instructions (e.g., software applications, programs, functions, and the like). Examples of the computer-readable storage memory 912 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations.

The computer-readable storage memory 912 provides storage of the device data 906 and various device applications 914, such as an operating system that is maintained as a software application with the computer-readable storage memory and executed by the processing system 910. In this example, the device applications include an object detection application 916 that implements embodiments of object presence and condition detection, such as when the example device 902 is implemented as the computing device 502 shown in FIG. 5. An example of the object detection application 916 is the object detection application 506 that is implemented by the computing device 502, as described with reference to FIGS. 5 and 6.

The device 902 also includes an audio and/or video system 918 that generates audio data for an audio device 920 and/or generates display data for a display device 922. The audio device and/or the display device include any devices that process, display, and/or otherwise render audio, video, display, and/or image data. In implementations, the audio device and/or the display device are integrated components of the example device 902. Alternatively, the audio device and/or the display device are external, peripheral components to the example device.

In embodiments, at least part of the techniques described for object presence and condition detection may be implemented in a distributed system, such as over a "cloud" 924 in a platform 926. The cloud 924 includes and/or is representative of the platform 926 for services 928 and/or resources 930. For example, the services 928 and/or the resources 930 may include the object detection application, as well as the various object presences and detection data.

The platform 926 abstracts underlying functionality of hardware, such as server devices (e.g., included in the services 928) and/or software resources (e.g., included as the resources 930), and connects the example device 902 with other devices, servers, etc. The resources 930 may also include applications and/or data that can be utilized while computer processing is executed on servers that are remote from the example device 902. Additionally, the services 928 and/or the resources 930 may facilitate subscriber network services, such as over the Internet, a cellular network, or Wi-Fi network. The platform 926 may also serve to abstract and scale resources to service a demand for the resources 930 that are implemented via the platform, such as in an interconnected device embodiment with functionality distributed throughout the system 900. For example, the functionality may be implemented in part at the example device 902 as well as via the platform 926 that abstracts the functionality of the cloud 924.

Although embodiments of object presence and condition detection have been described in language specific to features and/or methods, the appended claims are not necessarily limited to the specific features or methods described. Rather, the specific features and methods are disclosed as example implementations of object presence and condition detection.

The invention claimed is:

1. A method, comprising:
   emitting light that is directed to pass through a translucent object, the light directed at a first edge of the translucent object along its thickness;
   detecting an intensity of the light proximate an opposing, second edge of the translucent object;
   determining a presence of the translucent object based on the detected intensity of the light that passes through the translucent object, the detected intensity of the light that passes through the translucent object is relative and indicates one of:
   the presence of the translucent object based on a lower intensity of the light; or
   the translucent object is not present based on a higher intensity of the light.

2. The method as recited in claim 1, wherein the translucent object is an optic lens, and said emitting the light is directed to pass through along a diameter of the optic lens and perpendicular to an axis of the optic lens.

3. The method as recited in claim 1, further comprising:
   determining a condition of the translucent object based on the detected intensity of the light that passes through the translucent object.

4. The method as recited in claim 3, further comprising:
   directing a laser light through optic surfaces of the translucent object with a laser; and
   continuously said determining the presence and the condition of the translucent object to prevent shut-off of said directing the laser light through the translucent object.

5. The method as recited in claim 4, further comprising:
   shutting-off the laser light responsive to determining a damaged condition of the translucent object.

6. The method as recited in claim 1, wherein the translucent object is a multi-lens array, and said emitting the light that is directed at the first edge of the multi-lens array to pass through to the opposing, second edge of the multi-lens array.

7. The method as recited in claim 6, wherein the detected intensity of the light indicates that the multi-lens array has been installed upside down.

8. The method as recited in claim 1, wherein the detected intensity of the light indicates a damaged condition of the translucent object.

9. The method as recited in claim 1, further comprising:
   receiving a voltage signal from a light detector that detects the intensity of the light that passes through the translucent object, and said determining the presence of the translucent object based on the voltage signal that corresponds to the detected intensity of the light.

10. The method as recited in claim 9, wherein the presence of the translucent object is determined based on the voltage signal being:
    one of above or below a voltage comparison threshold; or
    comparable to a light emission signature of the translucent object, the light emission signature of the translucent object calibrated with the light detector when the translucent object is in an operable condition.

11. A system, comprising:
    a light emitter configured to emit light that is directed to pass through a translucent object, the light directed at a first edge of the translucent object along its thickness;
    a light detector configured to detect an intensity of the light proximate an opposing, second edge of the translucent object along its thickness, a presence of the translucent object determinable based on the detected intensity of the light that passes through the translucent object, the detected intensity of the light that passes through the translucent object relative and indicating one of:
    the presence of the translucent object based on a lower intensity of the light; or
    the translucent object is not present based on a higher intensity of light.

12. The system as recited in claim 11, further comprising:
    a memory and processing system to implement an object detection application that is configured to:
    receive a voltage signal from the light detector, the voltage signal corresponding to the detected intensity of the light that passes through the translucent object; and
    determine the presence of the translucent object based on the received voltage signal.

13. The system as recited in claim 12, wherein the object detection application is configured to determine the presence of the translucent object based on the voltage signal being:
    one of above or below a voltage comparison threshold; or
    comparable to a light emission signature of the translucent object, the light emission signature of the translucent object calibrated with the light detector.

14. The system as recited in claim 12, further comprising:
    a laser configured to direct a laser light through optic surfaces of the translucent object; and wherein:

the object detection application is configured to continuously determine the presence and the condition of the lens to prevent shut-off of the laser light being directed through the translucent object.

15. The system as recited in claim 14, further comprising:
a shut-off switch configured to shut-off the laser responsive to receiving an indication of an inoperable condition of the translucent object from the object detection application.

16. The system as recited in claim 11, wherein the translucent object is a multi-lens array and the light is directed at the first edge of the multi-lens array to pass through to the opposing, second edge of multi-lens array.

17. The system as recited in claim 16, wherein the detected intensity of the light indicates that the multi-lens array has been installed upside down.

18. A system, comprising:
a laser configured to direct a laser light through optic surfaces of translucent objects that are implemented in a stacked configuration; and
a memory and processing system to implement an object detection application that is configured to continuously determine a presence and a condition of the translucent objects to prevent shut-off of the laser light being directed through the optic surfaces of the translucent objects.

19. The system as recited in claim 18, wherein:
each one of the translucent objects has an associated set of light emitter and light detector components;
an associated light emitter configured to emit a light along a diameter of a respective translucent object perpendicular to the optic surface of the translucent object; and
an associated light detector configured to detect the intensity of the light that passes through the respective translucent object.

20. The system as recited in claim 19, wherein the detected intensity of the light that passes through the respective translucent object is relative and indicates one of:
the presence of the respective translucent object based on a lower intensity of the light; or
the respective translucent object is not present based on a higher intensity of the light.

* * * * *